US012285536B2

(12) United States Patent
Schmalenberg et al.

(10) Patent No.: US 12,285,536 B2
(45) Date of Patent: Apr. 29, 2025

(54) VEHICLE CLEANING SUBSYSTEM AND METHOD OF CLEANING A VEHICLE

(71) Applicant: Toyota Motor Engineering & Manufacturing North America, Inc, Plano, TX (US)

(72) Inventors: Paul D. Schmalenberg, Pittsburgh, PA (US); Frederico Marcolino Quintao Severgnini, Ann Arbor, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 946 days.

(21) Appl. No.: 17/220,997

(22) Filed: Apr. 2, 2021

(65) Prior Publication Data

US 2022/0313859 A1    Oct. 6, 2022

(51) Int. Cl.
*A61L 2/28* (2006.01)
*A61L 2/08* (2006.01)
*A61L 2/24* (2006.01)
*G01N 21/88* (2006.01)

(52) U.S. Cl.
CPC .................................. *A61L 2/28* (2013.01); *A61L 2/08* (2013.01); *A61L 2/24* (2013.01); *G01N 21/88* (2013.01); *A61L 2202/14* (2013.01); *A61L 2202/25* (2013.01)

(58) Field of Classification Search
CPC .... G01N 21/55; G01N 21/88; G01N 21/8806; G01N 21/9018; G01N 21/9036; G01N 2021/4153
See application file for complete search history.

(56) References Cited

U.S. PATENT DOCUMENTS

| | | | | |
|---|---|---|---|---|
| 2,730,922 A * | 1/1956 | Beard | ...................... | B08B 9/46 |
| | | | | 250/214 R |
| 4,967,238 A * | 10/1990 | Bares | ................. | G03G 21/0005 |
| | | | | 399/34 |
| 5,717,216 A | 2/1998 | McCoy et al. | | |
| 9,404,854 B2 * | 8/2016 | Hunt | .................... | G01N 21/636 |

(Continued)

FOREIGN PATENT DOCUMENTS

JP        5087068 B2    11/2012
JP     2017164674 A     9/2017

(Continued)

*Primary Examiner* — Jennifer Wecker
*Assistant Examiner* — Brady C Pilsbury
(74) *Attorney, Agent, or Firm* — Jordan IP Law, LLC

(57) ABSTRACT

A vehicle subsystem for cleaning a vehicle cabin may include one or more light sources, a sensor module, and a vehicle cleaning control module. The one or more light sources are mounted in the vehicle cabin to project a collimated beam of light to contact one or more target surfaces in the vehicle cabin. The sensor module includes an array of one or more sensors mounted adjacent to the one or more target surfaces, to detect as sensor data the light reflected from the one or more target surfaces. The vehicle cleaning control module includes one or more processors, coupled to the sensor module, to execute a set of instructions to conduct, in response to the detection, specular reflection analysis of the sensor data, and determine, in response to the specular reflection analysis, a state of cleanliness of the vehicle cabin.

17 Claims, 11 Drawing Sheets

(56) References Cited

U.S. PATENT DOCUMENTS

| | | | |
|---|---|---|---|
| 9,694,739 B2 | 7/2017 | Salter et al. | |
| 2001/0043330 A1* | 11/2001 | Jung | G01J 3/0216 |
| | | | 356/73 |
| 2003/0067502 A1* | 4/2003 | Arquilevich | B41J 2/125 |
| | | | 347/19 |
| 2004/0048131 A1* | 3/2004 | Canepa | G01M 3/025 |
| | | | 429/492 |
| 2006/0054836 A1* | 3/2006 | Tezuka | G01N 21/9505 |
| | | | 250/372 |
| 2018/0164213 A1* | 6/2018 | Windorfer | G01N 21/251 |
| 2018/0339075 A1 | 11/2018 | Kennedy et al. | |
| 2020/0061223 A1* | 2/2020 | Hallack | B60N 2/002 |

FOREIGN PATENT DOCUMENTS

| | | |
|---|---|---|
| JP | 2018173299 A | 11/2018 |
| TW | M447343 U | 2/2013 |

\* cited by examiner

VEHICLE CLEANING SUBSYSTEM AND METHOD OF CLEANING A VEHICLE

TECHNICAL FIELD

Embodiments relate generally to a vehicle sanitizer subsystem, and one or more methods of cleaning a vehicle.

BACKGROUND

Ultraviolet (UV) light emission is a known technology used to clean the inside surfaces of a vehicle by killing bacteria and viruses. Although UV lights are used to clean surfaces within the vehicle cabin, they do not always reach hard-to-reach spaces or clean deep stains. Passengers may enter a vehicle and notice that there are some areas of a vehicle that aren't actually clean or adequately clean, even though UV lights had been activated prior to entering.

Traditional sensors used to detect dirt, debris, trash, spills, etc., within a vehicle cabin cannot detect undesirable fluids such as lubricants or grease that has been built up on metal surfaces in the vehicle cabin, such as, for example door handles, since lubricants and grease are often times the same color as the surface upon which it rests.

BRIEF SUMMARY

Within a vehicle cabin, surfaces may become unclean and/or unsanitary due to the presence of undesirable particles, debris, fluids, etc. thereon. In accordance with one or more embodiments, a vehicle sanitizer subsystem and method of cleaning a vehicle are provided to determine the presence of such undesirable particles, debris, fluids, etc. and then make a determination as to the cleanliness of the surface based on specular reflection analysis.

In accordance with one or more embodiments, when a collimated beam of light is projected to contact one or more target surfaces in the vehicle cabin, the presence of undesirable particles, debris, fluids, etc. will cause diffusion of the light (i.e., scattering of light) that will be detected or captured by an array of sensors mounted adjacent to the one or more target surfaces. Particularly, due to the specific arrangement of sensors in the sensor array, a greater intensity of reflective light will be detected or captured by certain sensors (e.g., outer sensors) and less so for other sensors (e.g., inner sensors). Such light diffusion will be indicative of a non-clean surface.

On the other hand, should the one or more target surfaces have a relatively smooth surface, the light will have minimal to substantially no diffusion. Particularly, due to the specific arrangement of sensors in the sensor array, a greater intensity of reflective light will be detected or captured by certain sensors (e.g., inner sensors) and less so for other sensors (e.g., outer sensors). Such a lack of light diffusion will be indicative of a clean surface.

In accordance with one or more embodiments, the one or more target surfaces should be composed of a material having a reflective surface that permits specular reflection when light is projected thereon. The one or more target surfaces can comprise in whole or in part a metal surface, a glass surface, etc.

In accordance with one or more embodiments, a subsystem for cleaning a vehicle cabin comprises one or more of the following: one or more light sources mounted in the vehicle cabin to project a collimated beam of light to contact one or more target surfaces in the vehicle cabin; a sensor module, comprising an array of one or more sensors, mounted adjacent to the one or more target surfaces, to detect as sensor data the light reflected from the one or more target surfaces; and a vehicle cleaning control module, comprising one or more processors, coupled to the sensor module, to execute a set of instructions to: conduct, in response to the detection, specular reflection analysis of the sensor data; and determine, in response to the specular reflection analysis, a state of cleanliness of the vehicle cabin.

In accordance with one or more embodiments of the subsystem, the one or more processors are to execute the set of instructions to determine the state of cleanliness of the vehicle cabin by conducting a comparison of an intensity of reflective light received by one or more inner sensors in the sensor array and an intensity of reflective light received by one or more outer sensors in the sensor array.

In accordance with one or more embodiments of the subsystem, the one or more processors are to execute the set of instructions to cause, in response to a determination that the intensity of reflective light received by the one or more inner sensors is less than the intensity of reflective light received by the one or more outer sensors, one or more of: generation of one or more of an audio alert, a visual alert, and a haptic alert, and implementation of a cleaning sequence at least on the one or more target surfaces.

In accordance with one or more embodiments of the subsystem, the one or more processors are to execute the set of instructions to determine the state of cleanliness of the vehicle cabin comprises conducting a comparison of an intensity of reflective light received by one or more inner sensors in the sensor array with a predetermined minimum threshold intensity.

In accordance with one or more embodiments of the subsystem, the one or more processors are to execute the set of instructions to cause, in response to a determination that the intensity of reflective light received by the one or more inner sensors is less than the predetermined minimum threshold intensity, one or more of: generation of one or more of an audio alert, a visual alert, and a haptic alert, and implementation of a cleaning sequence at least on the one or more target surfaces.

In accordance with one or more embodiments of the subsystem, the one or more processors are to execute the set of instructions to determine the state of cleanliness of the vehicle cabin by conducting a comparison of an intensity of reflective light received by one or more outer sensors in the sensor array with a predetermined maximum threshold intensity.

In accordance with one or more embodiments of the subsystem, the one or more processors are to execute the set of instructions to cause, in response to a determination that the intensity of reflective light received by the one or more outer sensors is greater than the predetermined minimum threshold intensity, one or more of: generation of one or more of an audio alert, a visual alert, and a haptic alert, and implementation of a cleaning sequence at least on the one or more target surfaces.

In accordance with one or more embodiments, a computer program product for a vehicle, the computer program product including at least one computer readable medium comprising a set of instructions, which when executed by one or more processors, cause the one or more processors to: cause projection of a collimated beam of light to contact one or more target surfaces of a vehicle cabin; cause detection of the light reflected from the one or more target surfaces; conduct, in response to the detection, specular reflection analysis of the sensor data; and determine, in response to the specular reflection analysis, a state of cleanliness of the vehicle cabin.

In accordance with one or more embodiments of the computer program, the one or more processors are to execute the set of instructions to determine the state of cleanliness of the vehicle cabin by conducting a comparison of an intensity of reflective light received by one or more inner sensors in a sensor array and an intensity of reflective light received by one or more outer sensors in the sensor array.

In accordance with one or more embodiments of the computer program, the one or more processors are to execute the set of instructions to cause, in response to a determination that the intensity of reflective light received by the one or more inner sensors is less than the intensity of reflective light received by the one or more outer sensors, one or more of: generation of one or more of an audio alert, a visual alert, and a haptic alert, and implementation of a cleaning sequence at least on the one or more target surfaces.

In accordance with one or more embodiments of the computer program, the one or more processors are to execute the set of instructions to determine the state of cleanliness of the vehicle cabin comprises conducting a comparison of an intensity of reflective light received by one or more inner sensors in the sensor array with a predetermined minimum threshold intensity.

In accordance with one or more embodiments of the computer program, the one or more processors are to execute the set of instructions to cause, in response to a determination that the intensity of reflective light received by the one or more inner sensors is less than the predetermined minimum threshold intensity, one or more of: generation of one or more of an audio alert, a visual alert, and a haptic alert, and implementation of a cleaning sequence at least on the one or more target surfaces.

In accordance with one or more embodiments of the computer program, the one or more processors are to execute the set of instructions to determine the state of cleanliness of the vehicle cabin by conducting a comparison of an intensity of reflective light received by one or more outer sensors in the sensor array with a predetermined maximum threshold intensity.

In accordance with one or more embodiments of the computer program, the one or more processors are to execute the set of instructions to cause, in response to a determination that the intensity of reflective light received by the one or more outer sensors is greater than the predetermined minimum threshold intensity, one or more of: generation of one or more of an audio alert, a visual alert, and a haptic alert, and implementation of a cleaning sequence at least on the one or more target surfaces.

In accordance with one or more embodiments, a method of cleaning a vehicle cabin comprises one or more of the following: causing projection of a collimated beam of light to contact one or more target surfaces of the vehicle cabin; causing detection of the light reflected from the one or more target surfaces; conducting, in response to the detection, specular reflection analysis of the sensor data; and determining, in response to the specular reflection analysis, a state of cleanliness of the vehicle cabin.

In accordance with one or more embodiments of the method, determining the state of cleanliness of the vehicle cabin comprises conducting a comparison of an intensity of reflective light received by one or more inner sensors in a sensor array and an intensity of reflective light received by one or more outer sensors in the sensor array.

In accordance with one or more embodiments of the method, further comprising causing, in response to a determination that the intensity of reflective light received by the one or more inner sensors is less than the intensity of reflective light received by the one or more outer sensors, one or more of: generating one or more of an audio alert, a visual alert, and a haptic alert, and implementing a cleaning sequence at least on the one or more target surfaces.

In accordance with one or more embodiments of the method, determining the state of cleanliness of the vehicle cabin comprises one or more of: conducting a comparison of an intensity of reflective light received by one or more inner sensors in a sensor array with a predetermined minimum threshold intensity, and conducting a comparison of an intensity of reflective light received by one or more outer sensors in a sensor array with a predetermined maximum threshold intensity.

In accordance with one or more embodiments of the method, further comprising causing, in response to a determination that the intensity of reflective light received by the one or more inner sensors is less than the predetermined minimum threshold intensity, one or more of: generating one or more of an audio alert, a visual alert, and a haptic alert, and implementing a cleaning sequence at least on the one or more target surfaces.

In accordance with one or more embodiments of the method, further comprising causing, in response to a determination that the intensity of reflective light received by the one or more outer sensors is greater than the predetermined minimum threshold intensity, one or more of: generating one or more of an audio alert, a visual alert, and a haptic alert, and implementing a cleaning sequence at least on the one or more target surfaces.

BRIEF DESCRIPTION OF THE SEVERAL VIEWS OF THE DRAWINGS

The various advantages of the embodiments of the present invention will become apparent to one skilled in the art by reading the following specification and appended claims, and by referencing the following drawings, in which:

DETAILED DESCRIPTION

Figure 1:
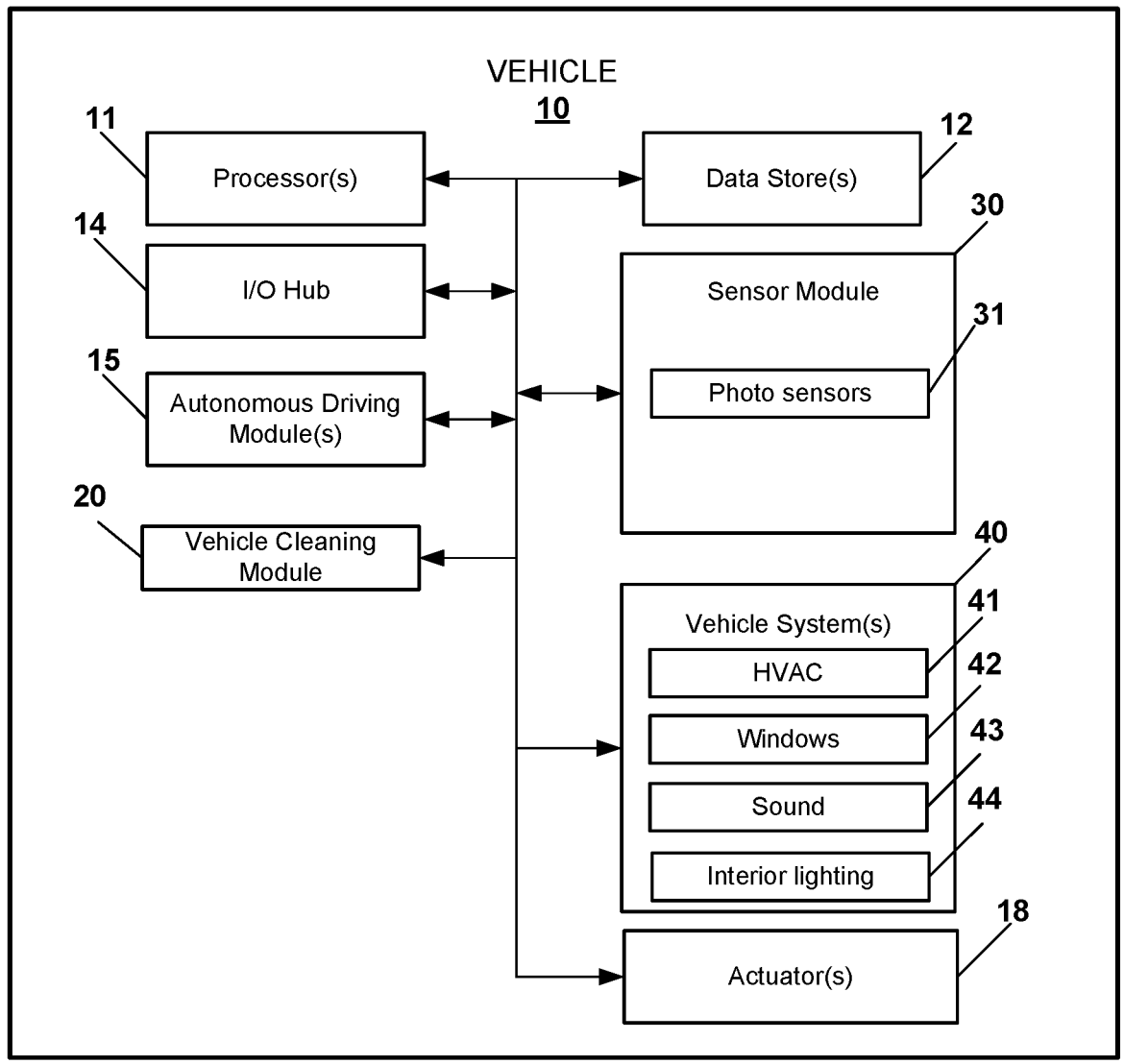
FIG. 1 illustrates an example vehicle, in accordance with one or more embodiments shown and described herein.

Turning to the figures, in which FIG. 1 illustrates a vehicle 10 that may comprise a mobility-as-a-service (MaaS) vehicle, a car, a truck, a van, a sport utility vehicle, a bus, etc. Embodiments, however, are not limited thereto, and thus, this disclosure contemplates the vehicle 10 comprising any suitable vehicle that falls within the spirit and scope of the principles of this disclosure. For example, the vehicle 10 may comprise a marine vehicle, an air vehicle, a space vehicle, or any other form of transport vehicle.

In accordance with one or more embodiments, the vehicle 10 may comprise one or more operational elements, some of which may be a part of an autonomous driving system. Some of the possible operational elements of the vehicle 10 are shown in FIG. 1 and will now be described. It will be understood that it is not necessary for the vehicle 10 to have all the elements illustrated in FIG. 1 and/or described herein. The vehicle 10 may have any combination of the various elements illustrated in FIG. 1. Moreover, the vehicle 10 may have additional elements to those illustrated in FIG. 1.

In accordance with one or more embodiments, the vehicle 10 may not include one or more of the elements shown in FIG. 1. Moreover, while the various operational elements are illustrated as being located within the vehicle 10, embodiments are not limited thereto, and thus, one or more of the operational elements may be located external to the vehicle 10, and even physically separated by large spatial distances.

In accordance with one or more embodiments, the vehicle 10 comprises one or more processors 11. As set forth, described, and/or illustrated herein, "processor" means any component or group of components that are configured to execute any of the processes described herein or any form of instructions to carry out such processes or cause such processes to be performed. The processors 11 may be implemented with one or more general-purpose and/or one or more special-purpose processors. Examples of suitable processors include graphics processors, microprocessors, microcontrollers, DSP processors, and other circuitry that may execute software. Further examples of suitable processors include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller. The processors 11 may comprise at least one hardware circuit (e.g., an integrated circuit) configured to carry out instructions contained in program code. In embodiments in which there is a plurality of processors 11, such processors 11 may work independently from each other, or one or more processors may work in combination with each other. In accordance with one or more embodiments, the processors 11 may be a host, main, or primary processor of the vehicle 10. For instance, the processors 11 may comprise an engine control unit (ECU).

In accordance with one or more embodiments, the vehicle 10 may comprise an I/O hub 14 operatively connected to other systems and subsystems of the vehicle 10. The I/O hub 14 may comprise an input interface and an output interface. The input interface and the output interface may be integrated as a single, unitary interface, or alternatively, be separate as independent interfaces that are operatively connected.

In one or more embodiments, the input interface may be used by a user, such as, for example, an operator of the vehicle to create one or more calendar events to for automatic sanitization of the vehicle cabin. The input interface is defined herein as any device, component, system, subsystem, element, or arrangement or groups thereof that enable information/data to be entered in a machine. The input interface may receive an input from a vehicle occupant (e.g. a driver or a passenger) or a remote operator of the vehicle 10. In an example, the input interface may comprise a user interface (UI), graphical user interface (GUI) such as, for example, a display, human-machine interface (HMI), or the like. Embodiments, however, are not limited thereto, and thus, the input interface may comprise a keypad, touch screen, multi-touch screen, button, joystick, mouse, trackball, microphone and/or combinations thereof.

The output interface is defined herein as any device, component, system, subsystem, element, or arrangement or groups thereof that enable information/data to be presented to a vehicle occupant and/or remote operator of the vehicle 10. The output interface may be configured to present information/data to the vehicle occupant and/or the remote operator. The output interface may comprise one or more of a visual display or an audio display such as a microphone, earphone, and/or speaker. One or more components of the vehicle 10 may serve as both a component of the input interface and a component of the output interface.

In accordance with one or more embodiments, the vehicle 10 may comprise one or more data stores 12 for storing one or more types of data. The vehicle 10 may include interfaces that enable one or more systems thereof to manage, retrieve, modify, add, or delete, the data stored in the data stores 12. The data stores 12 may comprise volatile and/or non-volatile memory. Examples of suitable data stores 12 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data stores 12 may be a component of the processors 11, or alternatively, may be operatively connected to the processors 11 for use thereby. As set forth, described, and/or illustrated herein, "operatively connected" may include direct or indirect connections, including connections without direct physical contact.

In accordance with one or more embodiments, the vehicle 10 may comprise a sensor module 30 configured to, at least during operation of the vehicle 10, dynamically detect, capture, determine, assess, monitor, measure, quantify, and/or sense light in the vehicle cabin. As set forth, described, and/or illustrated herein, "sensor" means any device, component, system, and/or subsystem that can perform one or more of detecting, determining, assessing, monitoring, measuring, quantifying, and sensing something. The one or more sensors may be configured to detect, determine, assess, monitor, measure, quantify and/or sense in real-time. As set forth, described, and/or illustrated herein, "real-time" means a level of processing responsiveness that a user, system, or subsystem senses as sufficiently immediate for a particular process or determination to be made, or that enables the processor to keep up with some external process.

In accordance with one or more embodiments, the vehicle 10 may comprise the vehicle cleaning control module 20. Operation of the vehicle cleaning control module 20 may be implemented as computer readable program code that, when executed by a processor, implement one or more of the various processes set forth, described, and/or illustrated herein. The vehicle cleaning control module 20 may be a component of the processors 11, or alternatively, may be executed on and/or distributed among other processing systems to which the processors 11 are operatively connected. The vehicle cleaning control module 20 may include a set of logic instructions executable by the processors 11. Alternatively or additionally, the data stores 12 may contain such logic instructions. The logic instructions may include assembler instructions, instruction set architecture (ISA) instructions, machine instructions, machine dependent instructions, microcode, state-setting data, configuration data for integrated circuitry, state information that personalizes electronic circuitry and/or other structural components that are native to hardware (e.g., host processor, central processing unit/CPU, microcontroller, etc.).

In the illustrated one or more embodiments of FIG. 2 through 4, the vehicle cleaning control module 20 may be configured to facilitate cleaning of the vehicle cabin, as will be described in greater detail hereinafter. For example, the vehicle cleaning control module 20 may be configured to cause, via one or more light sources 44a, projection of a collimated beam of light L to contact one or more target surfaces TS of the vehicle cabin. The vehicle cleaning control module 20 may be configured to cause, via the one or more sensor arrays 31, detection of the light L reflected from the one or more target surfaces TS. The vehicle cleaning control module 20 may be configured to conduct, in response to the detection, specular reflection analysis of the sensor data. The vehicle cleaning control module 20 may then be configured to determine, in response to the specular reflection analysis, a state of cleanliness of the vehicle cabin TS.

The captured sensor data may be located in a vehicle image database of the data stores 12 or an external source (e.g., cloud-based data store(s)).

In accordance with one or more embodiments, one or more of the modules 15, 20 set forth, described, and/or illustrated herein may include artificial or computational intelligence elements, e.g., neural network, fuzzy logic, or other machine learning algorithms.

In accordance with one or more embodiment, the vehicle 10 may comprise one or more vehicle systems 40, including but not limited to an HVAC system 41, a windows system 42, a sound system 43, interior lighting system 44, etc. Embodiments, however, are not limited thereto, and thus, this disclosure contemplates the vehicle 10 comprising more, fewer, or different systems or subsystems. In the illustrated example of FIG. 4, one or more of the vehicle systems 40 may form a subsystem comprising, for example, sensor module 30, HVAC 41, and interior lighting 44, which are controlled by the vehicle cleaning control module 20 and/or the one or more processors 11.

In accordance with one or more embodiment, one or more of the processors 11, the autonomous driving module 15, and the vehicle cleaning control module 20 may be operatively connected to communicate with the various vehicle systems 40 and/or individual components thereof. For example, one or more of the processors 11 and the vehicle cleaning control module 20 may be in communication to send and/or receive information from the various vehicle systems 40 to control the lighting, movement, speed, maneuvering, heading, direction, etc. of the vehicle 10. One or more of the processors 11 and the vehicle cleaning control module 20 may control some or all of the vehicle systems 40, and thus, may be partially or fully autonomous.

The vehicle 10 may comprise one or more actuators 18, which may be any element or combination of elements configured to modify, adjust and/or alter one or more of the vehicle systems 40 or components thereof in response to receiving signals or other inputs from one or more of the processors 11, the autonomous driving module 15, and the vehicle cleaning control module 20. Any suitable actuator may be used. For instance, the one or more actuators 18 may comprise motors, pneumatic actuators, hydraulic pistons, relays, solenoids, and/or piezoelectric actuators, etc.

In accordance with one or more embodiments, the subsystem 50 for cleaning a vehicle cabin comprises the vehicle cleaning control module 20, the sensor module 30, and the one or more light sources 44a.

The one or more light sources 44a are mounted in the vehicle cabin to project a collimated beam of light L to contact one or more target surfaces TS in the vehicle cabin. In one or more embodiments, the one or more light sources 44a comprise a near-infrared light source having a predetermined narrow band wavelength of, for example, about 1300 nm.

The one or more light sources 44a may be fixed in a position in the vehicle cabin that does not change relative to the vehicle cabin. Alternatively or additionally, the one or more light sources 44a may be manually or automatically moveable so as to change position relative to the vehicle cabin in a manner which facilitates the projection of the collimated beam of light L in a manner that contacts one or more target surfaces TS.

In accordance with one or more embodiments, the one or more light sources 44a may work independently from each other, or alternatively, may work in combination with each other. The one or more light sources 44a may be used in any combination, and may be used redundantly.

In accordance with one or more embodiments, the one or more light sources 44a may be fixed in a position that does not change relative to the vehicle cabin. Alternatively or additionally, the one or more light sources 44a may be manually or automatically moveable so as to change position relative to the vehicle cabin in a manner which facilitates the capture of sensor data from different portions of the vehicle cabin. Such movement of the one or more light sources 44a may be achieved in any suitable manner, such as, for example, by rotation (about one or more rotational axes), by pivoting (about a pivot axis), by sliding (along an axis), and/or by extending (along an axis). The one or more light sources 44a (and/or the movement thereof) may be selectively controlled by one or more of the processors 11, the vehicle cleaning control module 20, and any one or more of the modules set forth, described, and/or illustrated herein.

In accordance with one or more embodiments, the sensor module 30 comprises one or more sensors spatially arranged in an array 31 configuration in close proximity or otherwise adjacent to a corresponding target surfaces TS to facilitate detection or capturing, as sensor data, of light reflected from the one or more target surfaces TS. In accordance with one or more embodiments, the sensor module 30 may be configured to detect the type of liquid (e.g., water, lubricant, etc.) is on the one or more target surfaces TS. The one or more target surfaces TS may be composed of a material having a reflective surface that permits specular reflection when light is projected thereon. The one or more target surfaces can comprise in whole or in part a metal surface, a glass surface, etc. that serve in whole or in part as various components located in the vehicle cable, such as, for example, door knobs, and UIs, etc. Embodiments are not limited thereto, and thus, this disclosure contemplates the target surfaces TS to include other surfaces in the vehicle cabin.

In accordance with one or more embodiments, the sensor array 31 comprises photosensors 31a, 31b, 31c, 31d. Embodiments, however, are not limited thereto. This disclosure contemplates the sensor array 31 comprising any suitable sensor architecture that permits practice of the one or more embodiments.

In accordance with one or more embodiments, the one or more photosensors 31a, 31b, 31c, 31d of the sensor array 31 may be configured to detect, determine, assess, monitor, measure, quantify, and/or sense light in the vehicle cabin. In accordance with one or more embodiments, to generate high-quality reading, the photosensors 31a, 31b, 31c, 31d of the sensor array 31 are configured to detect or capture light at the predetermined narrow band wavelength of the one or more light sources 44a, and reject all other wavelengths outside of this predetermined narrow band wavelength.

Figure 2:
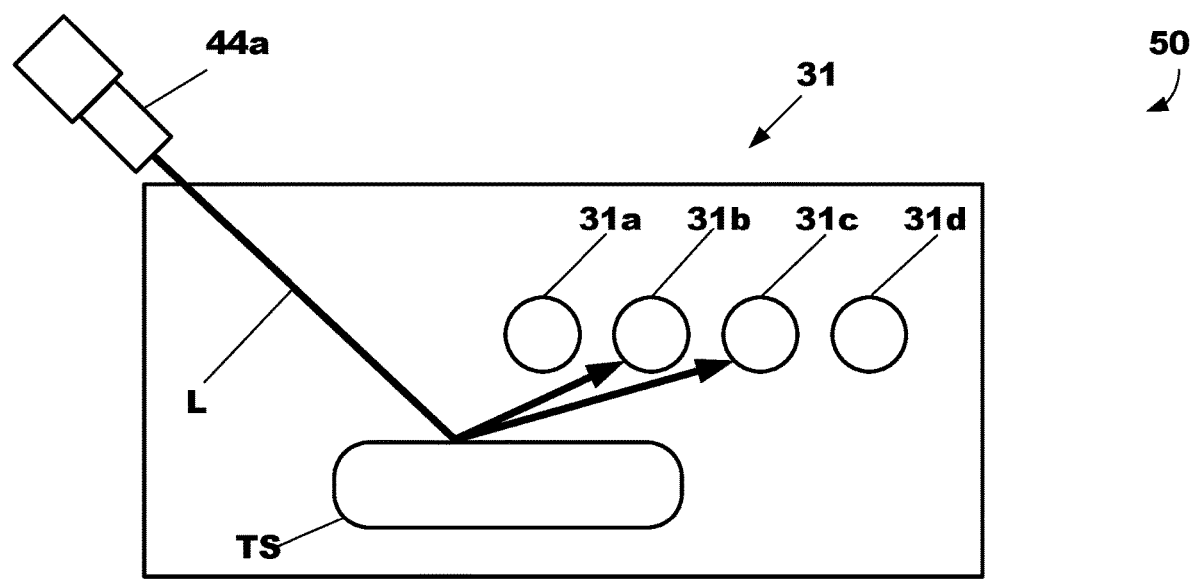
FIG. 2 illustrates an example vehicle cleaning subsystem, in accordance with one or more embodiments shown and described herein.
Figure 3:
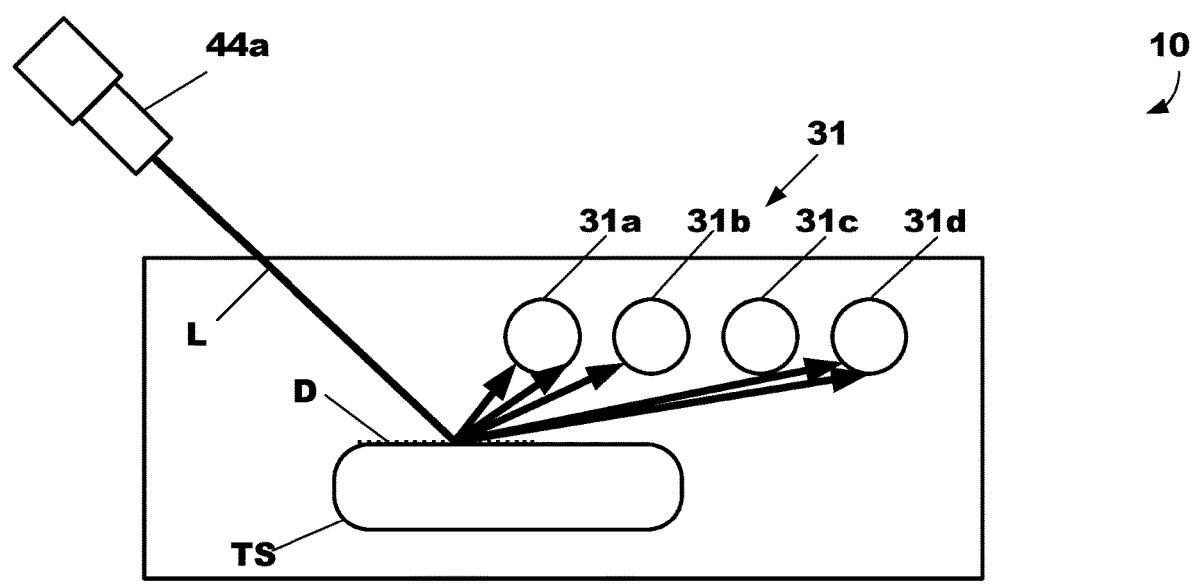
FIG. 3 illustrates an example of the vehicle cleaning subsystem of FIG. 1, in a deployed position.
Figure 4:
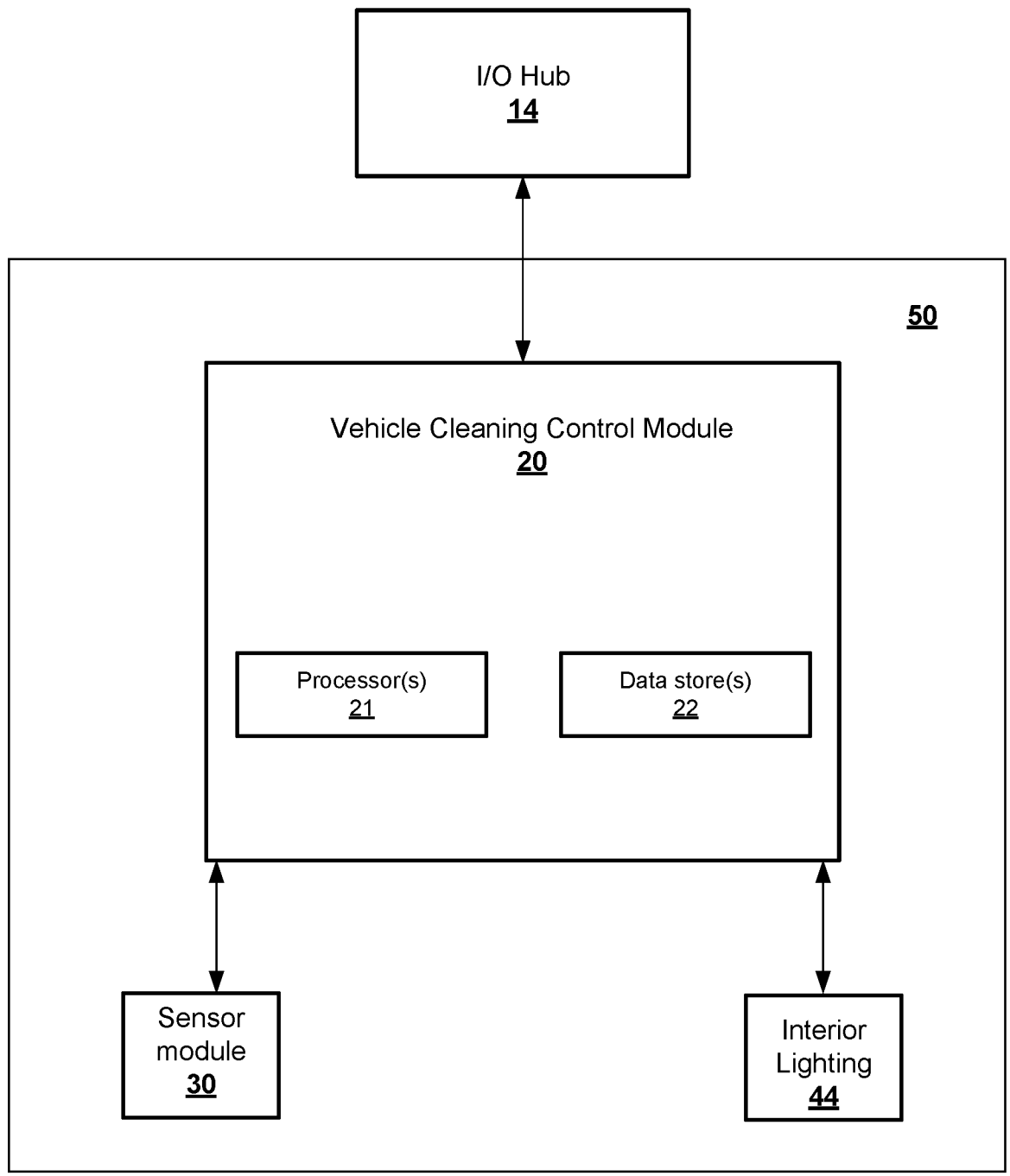
FIG. 4 illustrates an example vehicle subsystem that includes the vehicle cleaning control module, in accordance with one or more embodiments shown and described herein.

Although the illustrated one or more embodiments of FIGS. 2 and 3 illustrate a linear spatial configuration of the sensor array 31 that comprises one or more outer photosensors 31a, 31d and one or more inner photosensors 31b, 31c, embodiments are not limited thereto. This disclosure contemplates arranging the one or more photosensors 31a, 31b, 31c, 31d in a non-linear sensor array 31 spatial configuration that permits practice of the one or more embodiments.

In accordance with one or more embodiments, one or more of the sensor module 30, the sensor array 31, and the photosensors 31a, 31b, 31c, 31d may be operatively connected to the processors 11, the data stores 12, the autonomous driving module 15 and/or other elements, components, modules, systems, and subsystems of the vehicle 10. The sensor module 30, the sensor array 31, and any of the photosensors 31 described herein may be provided, positioned, or otherwise mounted in any suitable location with respect to the inside compartment of the vehicle cabin. Embodiments are not limited thereto, and thus, this disclosure contemplates the one or more photosensors 31a, 31b, 31c, 31d may be provided, positioned, or otherwise mounted in any suitable location that permits practice of the one or more embodiments.

In accordance with one or more embodiments, the one or more photosensors 31a, 31b, 31c, 31d of the sensor array 31 may work independently from each other, or alternatively, may work in combination with each other. The photosensors 31a, 31b, 31c, 31d may be used in any combination, and may be used redundantly to validate and improve the accuracy of the detection.

In accordance with one or more embodiments, the photosensors 31a, 31b, 31c, 31d may comprise one or more of a charge coupled device (CCD) sensor, a charge injection device (CID) sensor, and a complementary metal oxide semiconductor (CMOS) sensor. The photosensors 31a, 31b, 31c, 31d may detect or capture light of any suitable wavelength in one or more of the visible spectrum, near-infrared spectrum, and the infrared spectrum. The photosensors 31a, 31b, 31c, 31d may further comprise a filter to facilitate an absorption of light having a predetermined wavelength or a predetermined wavelengths range.

In accordance with one or more embodiments, the photosensors 31a, 31b, 31c, 31d may be fixed in a position that does not change relative to the vehicle cabin. Alternatively or additionally, the photosensors 31a, 31b, 31c, 31d may be manually or automatically moveable so as to change position relative to the vehicle cabin in a manner which facilitates the capture of sensor data from different portions of the vehicle cabin. Such movement of the photosensors 31a, 31b, 31c, 31d may be achieved in any suitable manner, such as, for example, by rotation (about one or more rotational axes), by pivoting (about a pivot axis), by sliding (along an axis), and/or by extending (along an axis). The photosensors 31a, 31b, 31c, 31d (and/or the movement thereof) may be selectively controlled by one or more of the processors 11, the vehicle cleaning control module 20, the sensor module 30, and any one or more of the modules set forth, described, and/or illustrated herein.

In accordance with one or more embodiments, the vehicle cleaning control module 20 comprises one or more processors 21, coupled to one or more data stores 22 and the sensor module 30, to execute a set of instructions stored in the one or more data stores 22 to conduct, in response to the detection by the one or more photosensors 31a, 31b, 31c, 31d, specular reflection analysis of the sensor data. The one or more processors 21 are to execute the set of instructions to determine, in response to the specular reflection analysis, a state of cleanliness of the vehicle cabin.

In accordance with one or more embodiments, the one or more processors 21 are to execute the set of instructions to determine the state of cleanliness of the vehicle cabin by conducting a comparison of an intensity of reflective light received by the one or more inner photosensors 31b, 31c in the sensor array 31 and an intensity of reflective light received by one or more outer photosensors 31a, 31d in the sensor array 31.

In the illustrated example of FIG. 3, the presence of undesirable items D such as, for example, particles, debris, fluids, etc. will cause diffusion of the light (i.e., scattering of light) that will be detected by the sensor array 31. Particularly, due to the specific arrangement of photosensors 31a, 31b, 31c, 31d in the sensor array 31, a greater intensity of reflected light will be detected or captured by the outer photosensors 31a, 31d. Such light diffusion will be indicative of a non-clean target surface TS.

On the other hand, in the illustrated example of FIG. 2, should the one or more target surfaces have a relatively smooth surface, the light will have minimal to substantially no diffusion. Particularly, due to the specific arrangement of photosensors 31a, 31b, 31c, 31d in the sensor array 31, a greater intensity of reflected light will be detected or captured by the inner photosensors 31b, 31c. Such a lack of light diffusion will be indicative of a clean target surface TS.

The one or more processors 21 are to execute the set of instructions to cause, in response to a determination that the intensity of reflective light received by the one or more inner sensors 31b, 31c is greater than the intensity of reflective light received by the one or more outer sensors 31a, 31d, generation of one or more of an audio alert, a visual alert, and a haptic alert. Alternatively or additionally, the one or more processors 21 are to execute the set of instructions to cause, in response to a determination that the intensity of reflective light received by the one or more inner sensors 31b, 31c is less than the intensity of reflective light received by the one or more outer sensors 31a, 31d, implementation of a cleaning sequence at least on the one or more target surfaces. Alternatively or additionally, the one or more processors 21 are to execute the set of instructions to cause, in response to a determination that the intensity of reflective light received by the one or more inner sensors 31b, 31c is less than the intensity of reflective light received by the one or more outer sensors 31a, 31d, transmission of a wireless signal or an electronic signal to a vehicle service center indicating the exact location(s) of the target surfaces that require cleaning.

In accordance with one or more embodiments, the one or more processors 21 are to execute the set of instructions to determine the state of cleanliness of the vehicle cabin TS by conducting a comparison of an intensity of reflective light L received by one or more inner sensors 31b, 31c in the sensor array 31 with a predetermined minimum threshold intensity. The one or more processors 21 are to execute the set of instructions to cause, in response to a determination that the intensity of reflective light L received by the one or more inner sensors 31b, 31c is less than the predetermined minimum threshold intensity, generation of one or more of an audio alert, a visual alert, and a haptic alert. Alternatively or additionally, the one or more processors 21 are to execute the set of instructions to cause, in response to a determination that the intensity of reflective light L received by the one or more inner sensors 31b, 31c is less than the predetermined minimum threshold intensity, implementation of a cleaning sequence at least on the one or more target surfaces TS. Alternatively or additionally, the one or more processors 21 are to execute the set of instructions to cause, in response to a determination that the intensity of reflective light L received by the one or more inner sensors 31b, 31c is less than the predetermined minimum threshold intensity, transmission of a wireless signal or an electronic signal to a vehicle service center indicating the exact location(s) of the target surfaces that require cleaning.

In accordance with one or more embodiments, the one or more processors 21 are to execute the set of instructions to determine the state of cleanliness of the vehicle cabin TS by conducting a comparison of an intensity of reflective light received by one or more outer sensors 31a, 31d in the sensor array 31 with a predetermined maximum threshold intensity. The one or more processors 21 are to execute the set of instructions to cause, in response to a determination that the intensity of reflective light received by the one or more outer sensors 31a, 31d is greater than the predetermined minimum threshold intensity, generation of one or more of an audio alert, a visual alert, and a haptic alert. Alternatively or additionally, the one or more processors 21 are to execute the set of instructions to cause, in response to a determination that the intensity of reflective light received by the one or more outer sensors 31a, 31d is greater than the predetermined minimum threshold intensity, implementation of a cleaning sequence at least on the one or more target surfaces. Alternatively or additionally, the one or more processors 21 are to execute the set of instructions to cause, in response to a determination that the intensity of reflective light received by the one or more outer sensors 31a, 31d is greater than the predetermined minimum threshold intensity, transmission of a wireless signal or an electronic signal to a vehicle service center indicating the exact location(s) of the target surfaces that require cleaning.

In the illustrated examples of FIGS. 5 to 11, a flowchart of methods 500 and 600 of sanitizing a vehicle. In one or more examples, the respective flowcharts of the methods 500, 600, 700, 800, 900, 1000, and 1100 may be implemented by the one or more processors 11, 21. For example, the one or more processors 11, 21 are configured to implement the methods 500, 600, 700, 800, 900, 1000, and 1100 using logic instructions (e.g., software), configurable logic, fixed-functionality hardware logic, etc., or any combination thereof. In one or more examples, software executed by the vehicle cleaning control module 20 provides functionality described or illustrated herein. In particular, software executing by the one or more processors 11, 21 is configured to perform one or more processing blocks of the methods 500, 600, 700, 800, 900, 1000, and 1100 set forth, described, and/or illustrated herein, or provides functionality set forth, described, and/or illustrated.

Figure 5:
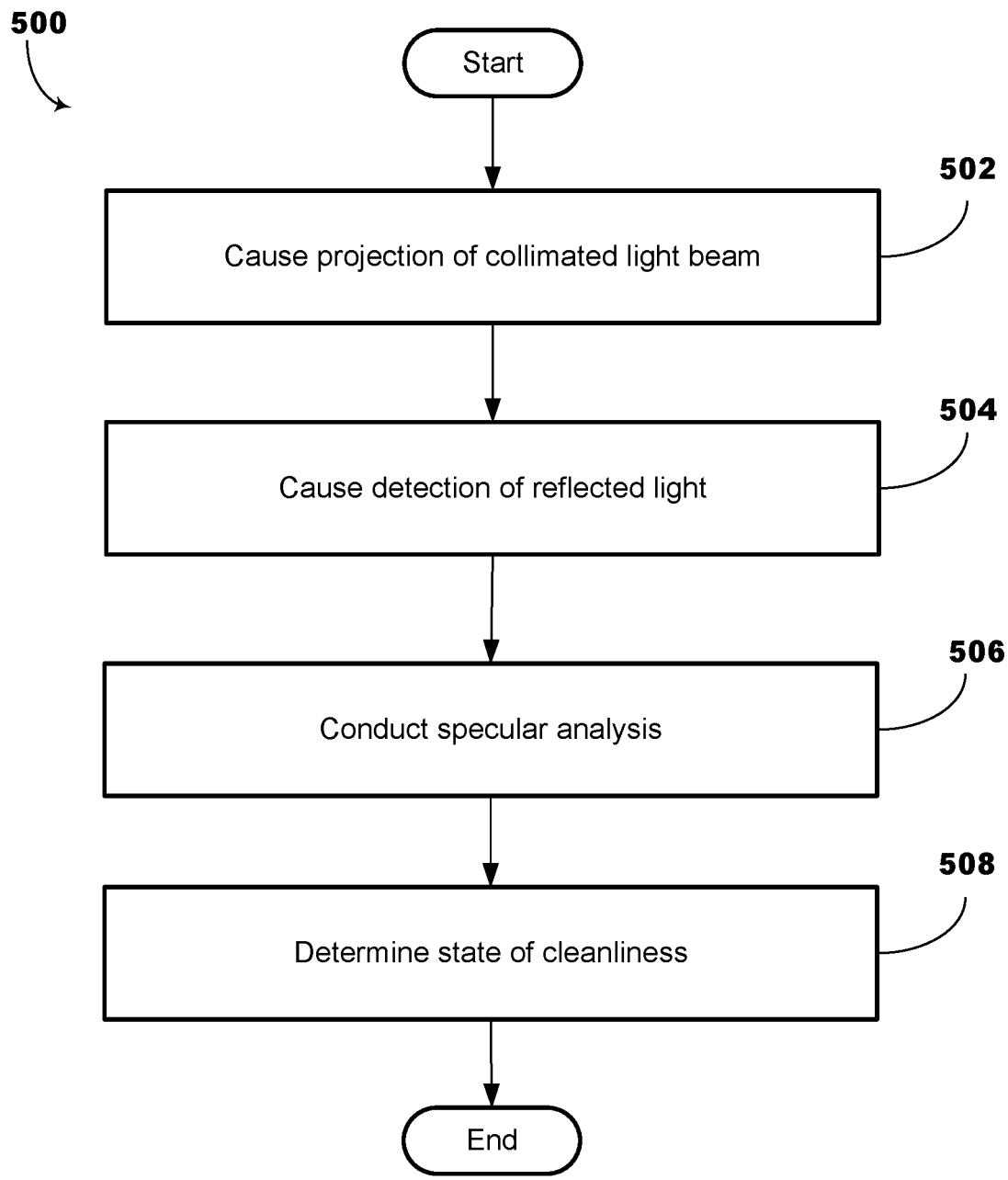
FIGS. 5 through 11 respectively illustrate a schematic diagram of example methods of sanitizing a vehicle, in accordance with one or more embodiments shown and described herein.

In the illustrated example of FIG. 5, illustrated process block 502 includes causing projection of a collimated beam of light to contact one or more target surfaces of a vehicle cabin.

The method 500 may then proceed to illustrated process block 504, which includes causing detection of the light reflected from the one or more target surfaces.

The method 500 may then proceed to illustrated process block 506, which includes conducting, in response to the detection, specular reflection analysis of the sensor data.

The method 500 may then proceed to illustrated process block 508, which includes determining, in response to the specular reflection analysis, a state of cleanliness of the vehicle cabin. The method 500 may terminate or end after execution of process block 508.

Figure 6:
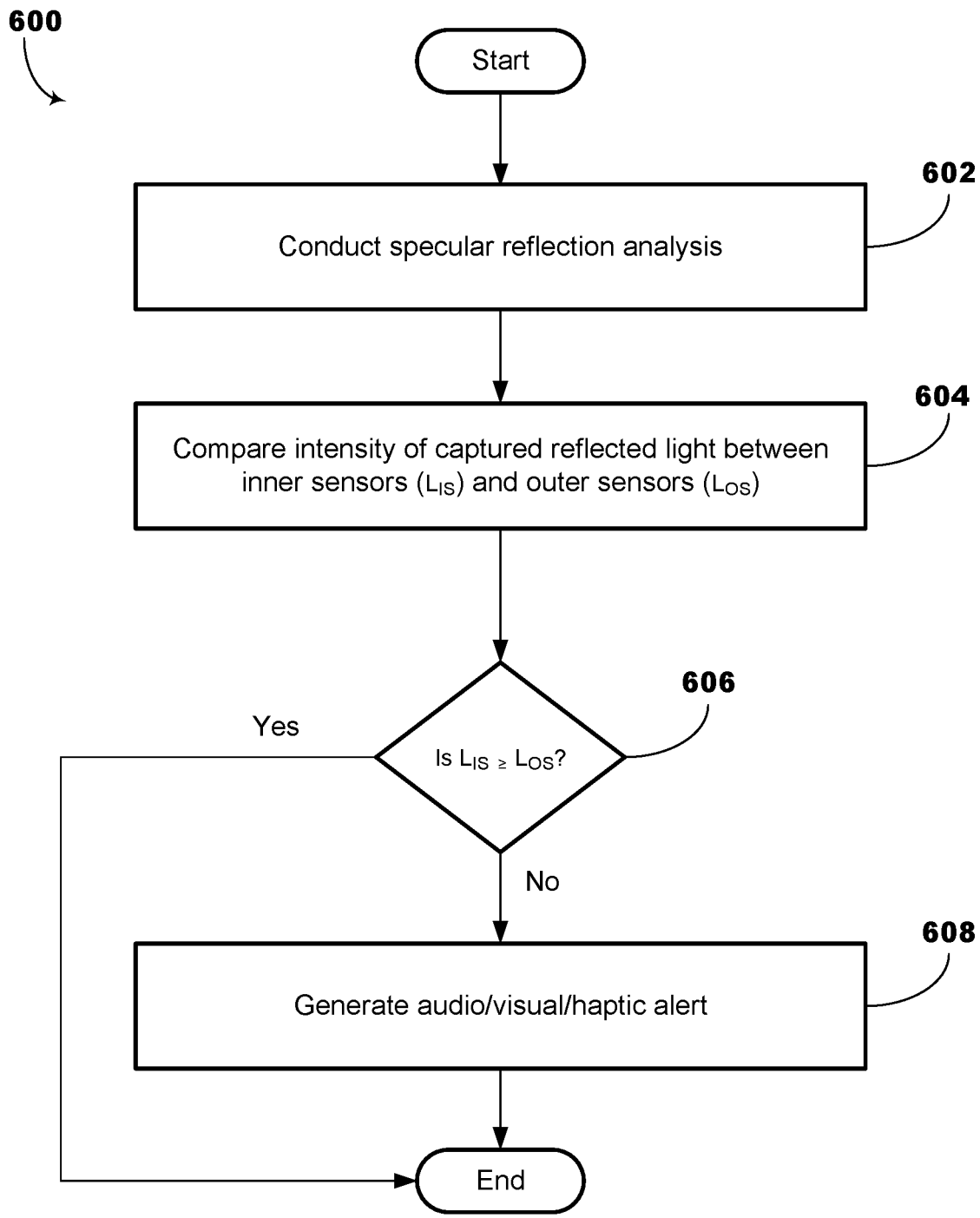

In the illustrated example of FIG. 6, illustrated process block 602 includes conducting a specular reflection analysis of sensor data in connection with a detection by a sensor array of light reflected from one or more target surfaces in a vehicle cabin.

The method 600 may then proceed to illustrated process block 604, which includes comparing, in response to the specular reflection analysis, the intensity of captured reflective light by one or more inner sensors $L_{IS}$ in the sensor array with the intensity of captured reflective light by one or more inner sensors $L_{OS}$ in the sensor array.

The method 600 may then proceed to illustrated process block 606, which includes determining whether the intensity of captured reflective light by the inner sensors $L_{IS}$ is greater than an intensity of captured reflective light by the outer sensors $L_{OS}$ in the sensor array.

If "Yes," the method 600 may terminate or end.

If "No," the method 600 may then proceed to illustrated process block 608, which includes generating one or more of an audio alert, a visual alert, and a haptic alert related to the state of cleanliness of the vehicle cabin. The method 600 may terminate or end after execution of process block 608.

Figure 7:
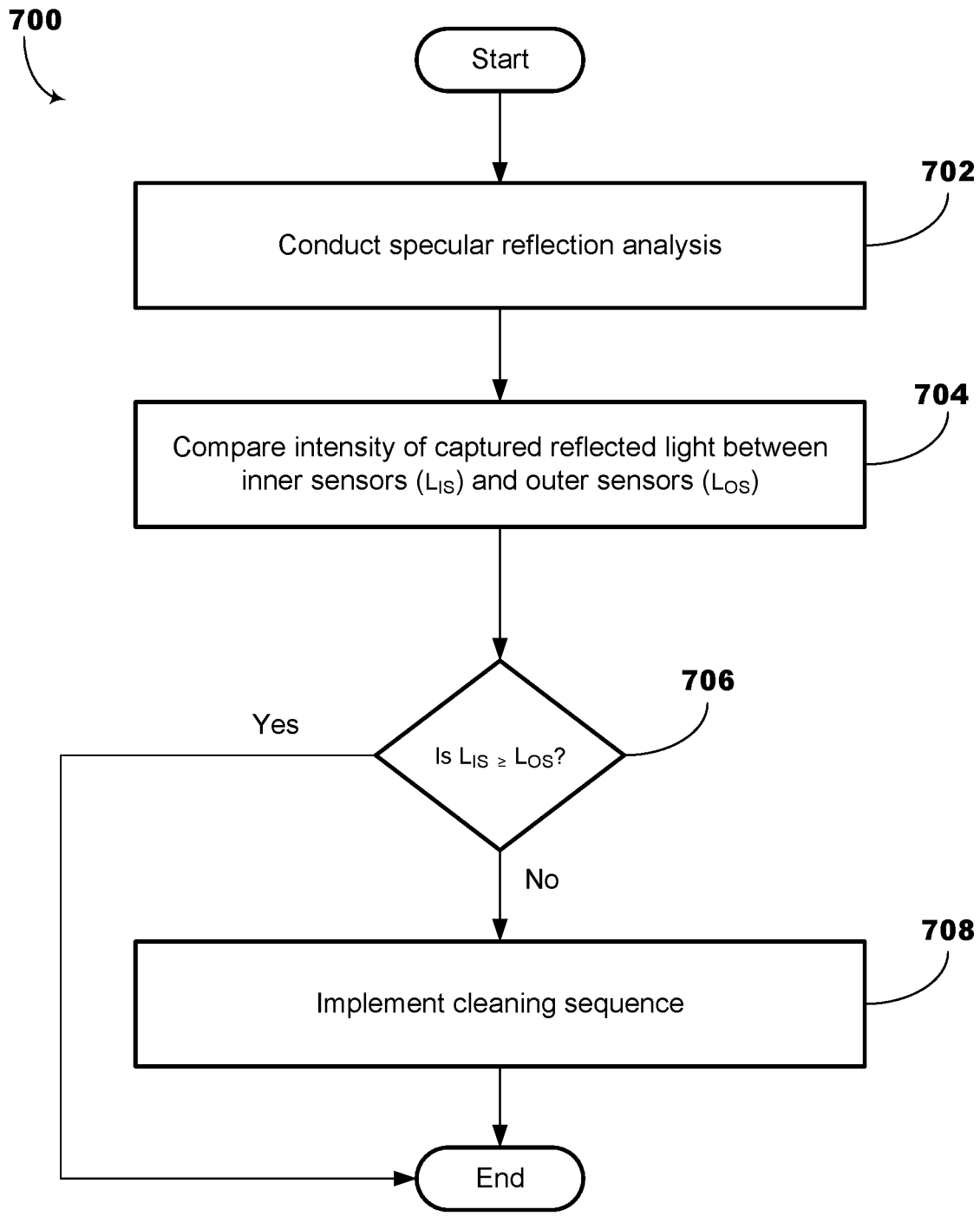

In the illustrated example of FIG. 7, illustrated process block 702 includes conducting a specular reflection analysis of sensor data in connection with a detection by a sensor array of light reflected from one or more target surfaces in a vehicle cabin.

The method 700 may then proceed to illustrated process block 704, which includes comparing, in response to the specular reflection analysis, the intensity of captured reflective light by one or more inner sensors $L_{IS}$ in the sensor array with the intensity of captured reflective light by one or more inner sensors $L_{OS}$ in the sensor array.

The method 700 may then proceed to illustrated process block 706, which includes determining whether the intensity of captured reflective light by the inner sensors $L_{IS}$ is greater than an intensity of captured reflective light by the outer sensors $L_{OS}$ in the sensor array.

If "Yes," the method 700 may terminate or end.

If "No," the method 700 may then proceed to illustrated process block 708, which includes implementing a cleaning sequence at least on the one or more target surfaces. The method 700 may terminate or end after execution of process block 708.

Figure 8:
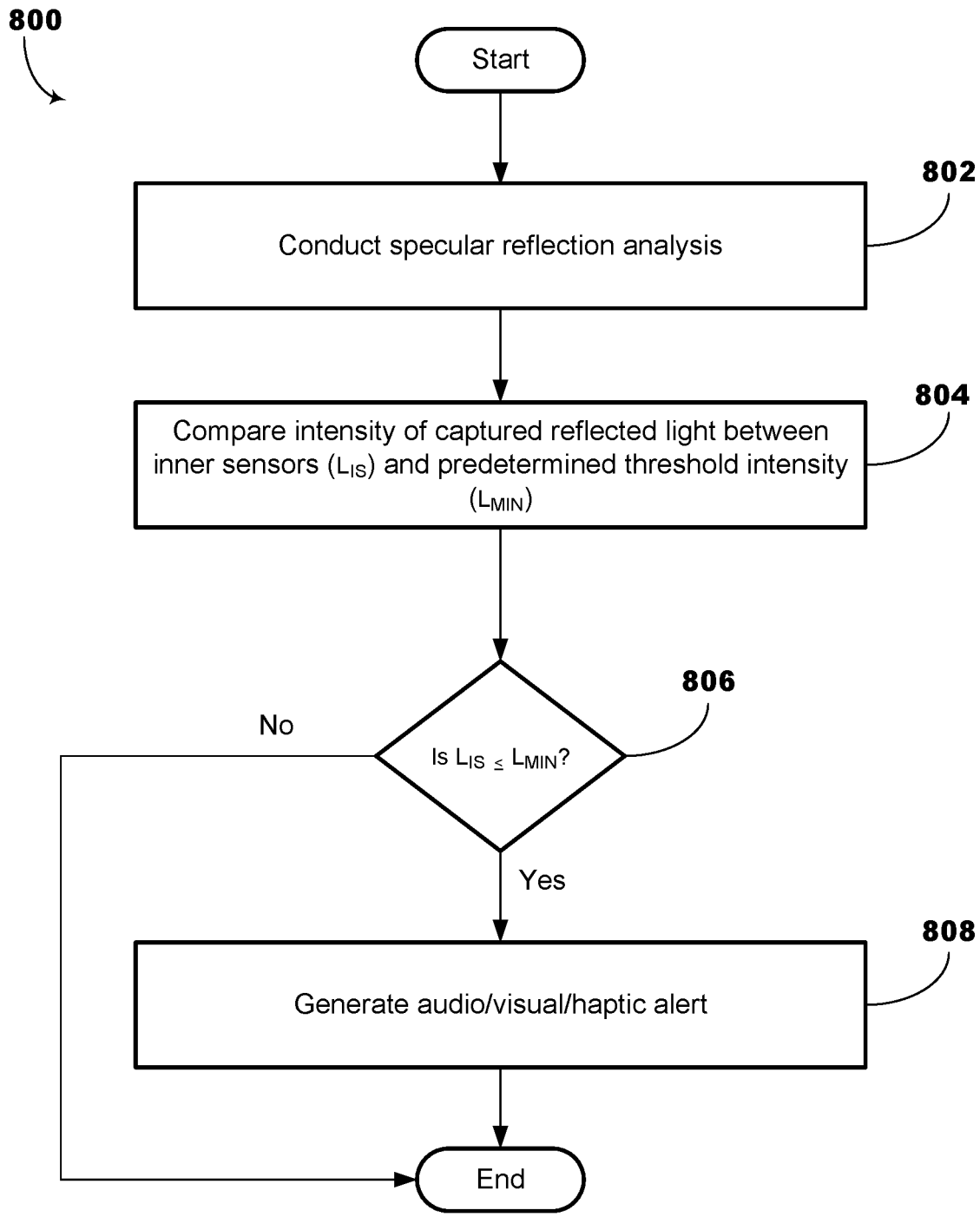

In the illustrated example of FIG. 8, illustrated process block 802 includes conducting a specular reflection analysis of sensor data in connection with a detection by a sensor array of light reflected from one or more target surfaces in a vehicle cabin.

The method 800 may then proceed to illustrated process block 804, which includes comparing, in response to the specular reflection analysis, the intensity of captured reflective light by one or more inner sensors $L_{IS}$ in the sensor array with a predetermined minimum threshold intensity $L_{MIN}$.

The method 800 may then proceed to illustrated process block 806, which includes a determination of whether the intensity of captured reflective light by the inner sensors $L_{IS}$ is less than the predetermined minimum threshold intensity $L_{MIN}$.

If "No," the method 800 may terminate or end.

If "Yes," the method 800 may then proceed to illustrated process block 808, which includes generating one or more of an audio alert, a visual alert, and a haptic alert related to the state of cleanliness of the vehicle cabin. The method 800 may terminate or end after execution of process block 808.

Figure 9:
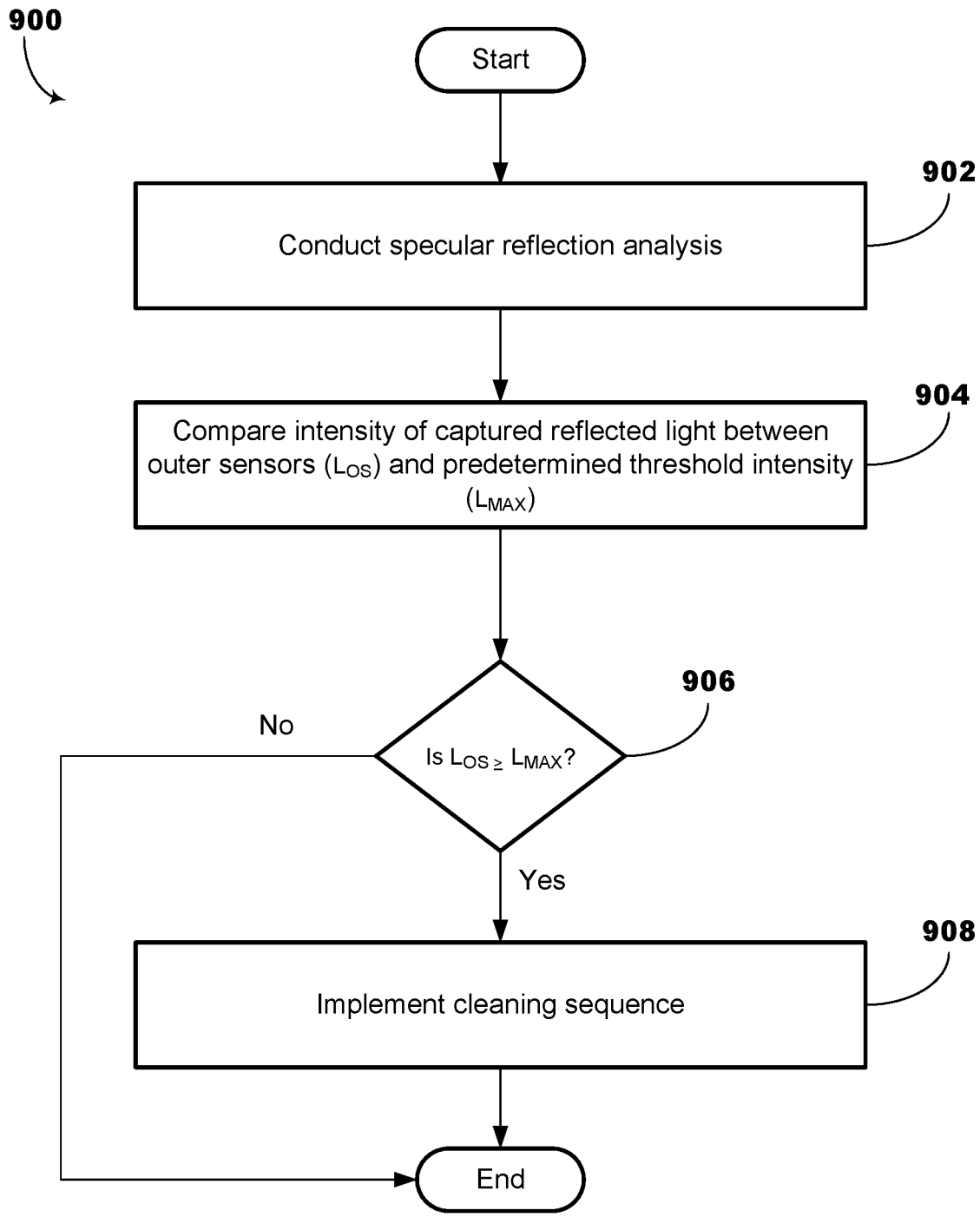

In the illustrated example of FIG. 9, illustrated process block 902 includes conducting a specular reflection analysis of sensor data in connection with a detection by a sensor array of light reflected from one or more target surfaces in a vehicle cabin.

The method 900 may then proceed to illustrated process block 904, which includes comparing, in response to the specular reflection analysis, the intensity of captured reflective light by one or more outer sensors $L_{OS}$ in the sensor array with a predetermined minimum threshold intensity $L_{MAX}$.

The method 900 may then proceed to illustrated process block 906, which includes a determination of whether the intensity of captured reflective light by the outer sensors $L_{OS}$ is greater than the predetermined maximum threshold intensity $L_{MAX}$.

If "No," the method 900 may terminate or end.

If "Yes," the method 900 may then proceed to illustrated process block 908, which includes implementing a cleaning sequence at least on the one or more target surfaces. The method 900 may terminate or end after execution of process block 908.

Figure 10:
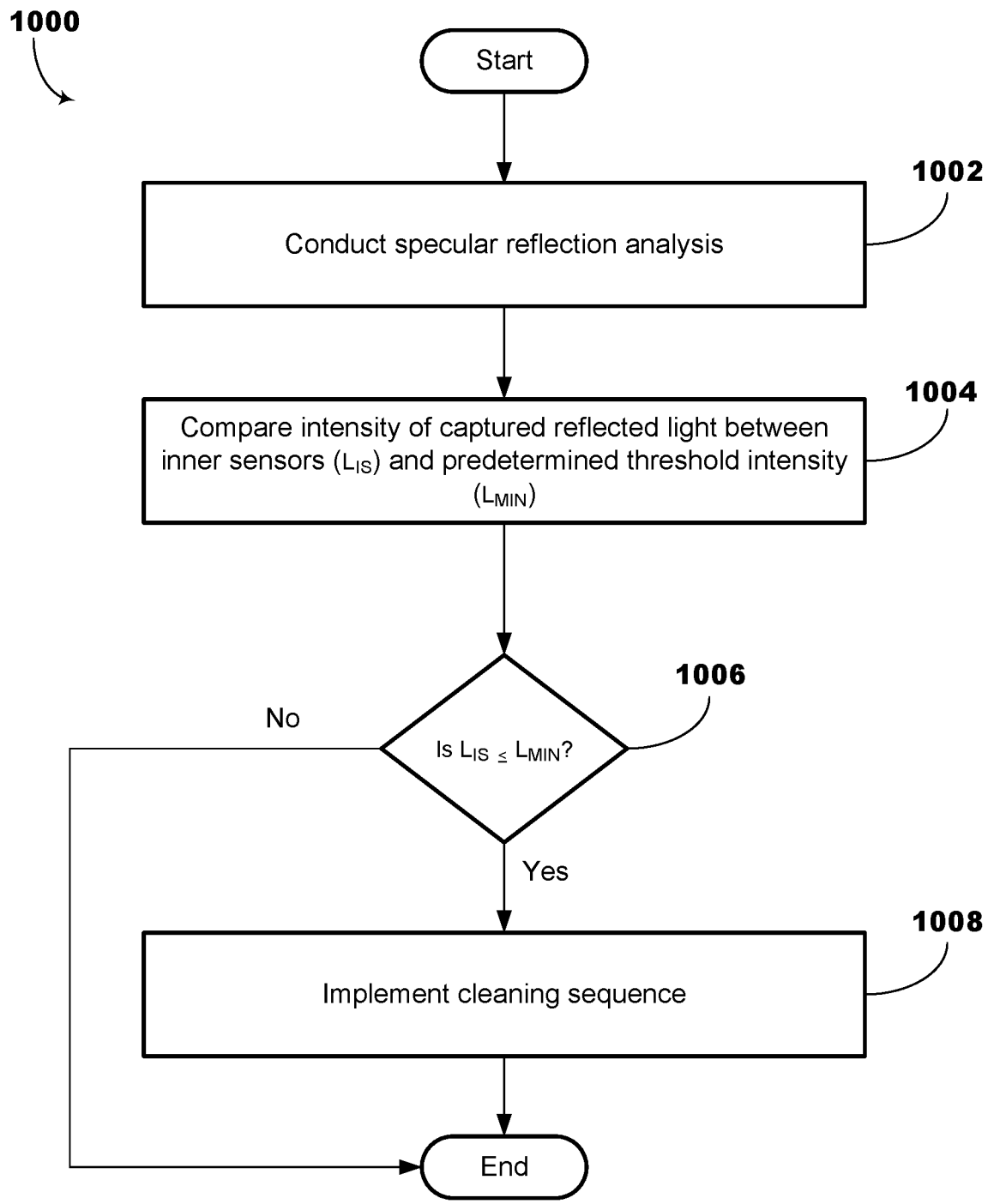

In the illustrated example of FIG. 10, illustrated process block 1002 includes conducting a specular reflection analysis of sensor data in connection with a detection by a sensor array of light reflected from one or more target surfaces in a vehicle cabin.

The method 1000 may then proceed to illustrated process block 1004, which includes comparing, in response to the specular reflection analysis, the intensity of captured reflective light by one or more inner sensors $L_{IS}$ in the sensor array with a predetermined minimum threshold intensity $L_{MIN}$.

The method 1000 may then proceed to illustrated process block 1006, which includes a determination of whether the intensity of captured reflective light by the inner sensors $L_{IS}$ is less than the predetermined minimum threshold intensity $L_{MIN}$.

If "No," the method 1000 may terminate or end.

If "Yes," the method 1000 may then proceed to illustrated process block 1008, which includes implementing a cleaning sequence at least on the one or more target surfaces. The method 1000 may terminate or end after execution of process block 1008.

Figure 11:
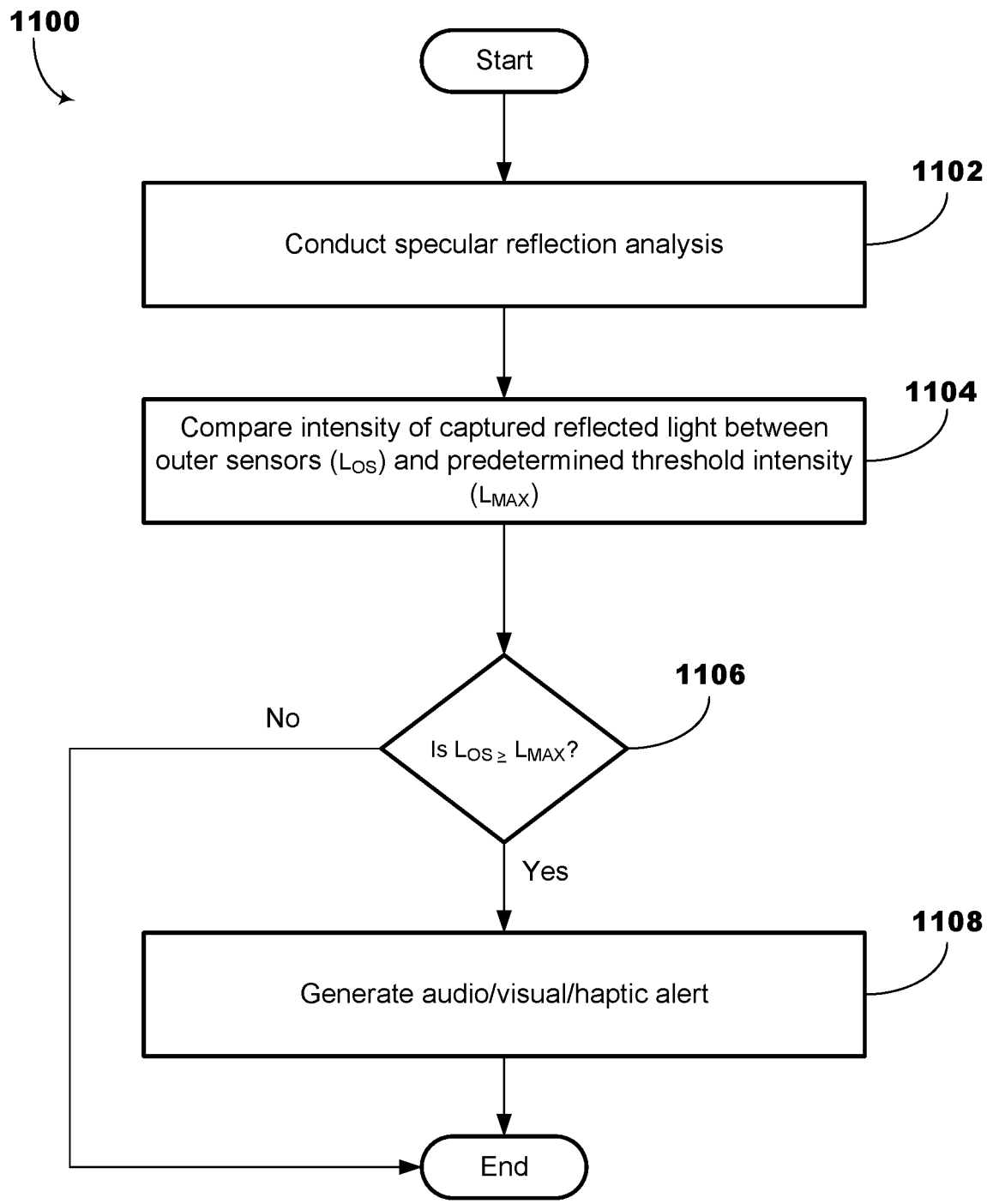

In the illustrated example of FIG. 11, illustrated process block 1102 includes conducting a specular reflection analysis of sensor data in connection with a detection by a sensor array of light reflected from one or more target surfaces in a vehicle cabin.

The method 1100 may then proceed to illustrated process block 1104, which includes comparing, in response to the specular reflection analysis, the intensity of captured reflective light by one or more outer sensors $L_{OS}$ in the sensor array with a predetermined maximum threshold intensity $L_{MAX}$.

The method 1100 may then proceed to illustrated process block 1106, which includes a determination of whether the intensity of captured reflective light by the outer sensors $L_{OS}$ is greater than the predetermined maximum threshold intensity $L_{MAX}$.

If "No," the method 1100 may terminate or end.

If "Yes," the method 1100 may then proceed to illustrated process block 1108, which includes implementing a cleaning sequence at least on the one or more target surfaces. The method 1100 may terminate or end after execution of process block 1108.

The terms "coupled," "attached," or "connected" may be used herein to refer to any type of relationship, direct or indirect, between the components in question, and may apply to electrical, mechanical, fluid, optical, electromagnetic, electromechanical or other connections. Additionally, the terms "first," "second," etc. are used herein only to facilitate discussion, and carry no particular temporal or chronological significance unless otherwise indicated. The terms "cause" or "causing" means to make, force, compel, direct, command, instruct, and/or enable an event or action to occur or at least be in a state where such event or action may occur, either in a direct or indirect manner.

Those skilled in the art will appreciate from the foregoing description that the broad techniques of the embodiments of the present invention may be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. A vehicle subsystem for cleaning one or more target surfaces in a vehicle cabin, the subsystem comprising:
   one or more light sources mounted in the vehicle cabin to project a collimated beam of light to contact the one or more target surfaces in the vehicle cabin;
   a sensor module, comprising an array of one or more sensors arranged in the vehicle cabin in a linear spatial configuration that includes one or more inner sensors and one or more outer sensors, mounted adjacent to the one or more target surfaces, to detect as sensor data the light reflected from the one or more target surfaces, wherein the one or more outer sensors are located at opposite ends of the linear spatial configuration and the one or more inner sensors are located between the one or more outer sensors; and
   a vehicle cleaning control module, comprising one or more processors, coupled to the sensor module, to execute a set of instructions to:
      conduct, in response to the detection, specular reflection analysis of the sensor data by comparing an intensity of reflective light received by the one or more inner sensors and an intensity of reflective light received by the one or more outer sensors; and
      determine, in response to the specular reflection analysis, a state of cleanliness of the vehicle cabin.

2. The vehicle subsystem of claim 1, wherein the one or more processors are to execute the set of instructions to cause, in response to a determination that the intensity of reflective light received by the one or more inner sensors is less than the intensity of reflective light received by the one or more outer sensors, one or more of:
   generation of one or more of an audio alert, a visual alert, and a haptic alert, and
   implementation of a cleaning sequence at least on the one or more target surfaces.

3. The vehicle subsystem of claim 1, wherein the one or more processors are to execute the set of instructions to determine the state of cleanliness of the vehicle cabin comprises conducting the comparison of the intensity of reflective light received by the one or more inner sensors in the sensor array with a predetermined minimum threshold intensity.

4. The vehicle subsystem of claim 3, wherein the one or more processors are to execute the set of instructions to cause, in response to a determination that the intensity of reflective light received by the one or more inner sensors is less than the predetermined minimum threshold intensity, one or more of:
 generation of one or more of an audio alert, a visual alert, and a haptic alert, and
 implementation of a cleaning sequence at least on the one or more target surfaces.

5. The vehicle subsystem of claim 1, wherein the one or more processors are to execute the set of instructions to determine the state of cleanliness of the vehicle cabin by conducting the comparison of the intensity of reflective light received by the one or more outer sensors in the sensor array with a predetermined maximum threshold intensity.

6. The vehicle subsystem of claim 5, wherein the one or more processors are to execute the set of instructions to cause, in response to a determination that the intensity of reflective light received by the one or more outer sensors is greater than the predetermined maximum threshold intensity, one or more of:
 generation of one or more of an audio alert, a visual alert, and a haptic alert, and
 implementation of a cleaning sequence at least on the one or more target surfaces.

7. A computer program product for a vehicle, the computer program product including at least one non-transitory computer readable medium comprising a set of instructions, which when executed by one or more processors, are configured to cause the one or more processors to:
 cause projection of a collimated beam of light to contact one or more target surfaces of a vehicle cabin;
 cause detection of the light reflected from the one or more target surfaces by a sensor module comprising an array of one or more sensors arranged in the vehicle cabin in a linear spatial configuration that includes one or more inner sensors and one or more outer sensors, mounted adjacent to the one or more target surfaces, wherein the one or more outer sensors are located at opposite ends of the linear spatial configuration and the one or more inner sensors are located between the one or more outer sensors;
 conduct, in response to the detection, specular reflection analysis of the sensor data by comparing an intensity of reflective light received by the one or more inner sensors and an intensity of reflective light received by the one or more outer sensors; and
 determine, in response to the specular reflection analysis, a state of cleanliness of the vehicle cabin.

8. The computer program product of claim 7, wherein the one or more processors are to execute the set of instructions to cause, in response to a determination that the intensity of reflective light received by the one or more inner sensors is less than the intensity of reflective light received by the one or more outer sensors, one or more of:
 generation of one or more of an audio alert, a visual alert, and a haptic alert, and
 implementation of a cleaning sequence at least on the one or more target surfaces.

9. The computer program product of claim 7, wherein the one or more processors are to execute the set of instructions to determine the state of cleanliness of the vehicle cabin comprises conducting the comparison of the intensity of reflective light received by the one or more inner sensors in the sensor array with a predetermined minimum threshold intensity.

10. The computer program product of claim 9, wherein the one or more processors are to execute the set of instructions to cause, in response to a determination that the intensity of reflective light received by the one or more inner sensors is less than the predetermined minimum threshold intensity, one or more of:
 generation of one or more of an audio alert, a visual alert, and a haptic alert, and
 implementation of a cleaning sequence at least on the one or more target surfaces.

11. The computer program product of claim 7, wherein the one or more processors are to execute the set of instructions to determine the state of cleanliness of the vehicle cabin by conducting the comparison of the intensity of reflective light received by the one or more outer sensors in the sensor array with a predetermined maximum threshold intensity.

12. The computer program product of claim 11, wherein the one or more processors are to execute the set of instructions to cause, in response to a determination that the intensity of reflective light received by the one or more outer sensors is greater than the predetermined maximum threshold intensity, one or more of:
 generation of one or more of an audio alert, a visual alert, and a haptic alert, and
 implementation of a cleaning sequence at least on the one or more target surfaces.

13. A method of cleaning one or more target surfaces in a vehicle cabin, the method comprising:
 causing projection of a collimated beam of light to contact the one or more target surfaces of the vehicle cabin;
 causing detection of the light reflected from the one or more target surfaces by a sensor module comprising an array of one or more sensors arranged in the vehicle cabin in a linear spatial configuration that includes one or more inner sensors and one or more outer sensors, mounted adjacent to the one or more target surfaces, wherein the one or more outer sensors are located at opposite ends of the linear spatial configuration and the one or more inner sensors are located between the one or more outer sensors;
 conducting, in response to the detection, specular reflection analysis of the sensor data by comparing an intensity of reflective light received by the one or more inner sensors and an intensity of reflective light received by the one or more outer sensors; and
 determining, in response to the specular reflection analysis, a state of cleanliness of the vehicle cabin.

14. The method of claim 13, further comprising causing, in response to a determination that the intensity of reflective light received by the one or more inner sensors is less than the intensity of reflective light received by the one or more outer sensors, one or more of:
 generating one or more of an audio alert, a visual alert, and a haptic alert, and
 implementing a cleaning sequence at least on the one or more target surfaces.

15. The method of claim 13, wherein determining the state of cleanliness of the vehicle cabin comprises one or more of:
 conducting the comparison of the intensity of reflective light received by the one or more inner sensors in the sensor array with a predetermined minimum threshold intensity, and
 conducting the comparison of the intensity of reflective light received by the one or more outer sensors in the sensor array with a predetermined maximum threshold intensity.

16. The method of claim 15, further comprising causing, in response to a determination that the intensity of reflective light received by the one or more inner sensors is less than the predetermined minimum threshold intensity, one or more of:
  generating one or more of an audio alert, a visual alert, and a haptic alert, and
  implementing a cleaning sequence at least on the one or more target surfaces.

17. The method of claim 15, further comprising causing, in response to a determination that the intensity of reflective light received by the one or more outer sensors is greater than the predetermined maximum threshold intensity, one or more of:
  generating one or more of an audio alert, a visual alert, and a haptic alert, and
  implementing a cleaning sequence at least on the one or more target surfaces.

* * * * *